(12) United States Patent
McKeon

(10) Patent No.: US 7,013,732 B2
(45) Date of Patent: Mar. 21, 2006

(54) METHOD AND APPARATUS FOR TEMPERATURE-CONTROLLED ULTRASONIC INSPECTION

(75) Inventor: James C. P. McKeon, Woodbridge, VA (US)

(73) Assignee: Sonix, Inc., Springfield, VA (US)

( * ) Notice: Subject to any disclaimer, the term of this patent is extended or adjusted under 35 U.S.C. 154(b) by 0 days.

(21) Appl. No.: 10/775,843

(22) Filed: Feb. 10, 2004

(65) Prior Publication Data

US 2004/0173024 A1    Sep. 9, 2004

Related U.S. Application Data

(60) Provisional application No. 60/448,622, filed on Feb. 19, 2003.

(51) Int. Cl.
*G01N 29/00* (2006.01)
(52) U.S. Cl. .................................................. 73/644
(58) Field of Classification Search ............ 73/644, 73/617
See application file for complete search history.

(56) References Cited

U.S. PATENT DOCUMENTS

| | | | |
|---|---|---|---|
| 3,063,290 A | 11/1962 | Kaserman et al. | |
| 3,737,573 A | 6/1973 | Kessler | |
| 3,790,281 A | 2/1974 | Kessler et al. | |
| 3,850,027 A | 11/1974 | Nakanishi et al. | |
| 3,886,793 A | 6/1975 | Cramer et al. | |
| 3,898,839 A | 8/1975 | White | |
| 4,008,602 A | 2/1977 | Love | |
| 4,012,951 A | 3/1977 | Kessler | |
| 4,058,000 A * | 11/1977 | Ries et al. | 73/644 |
| 4,164,150 A * | 8/1979 | Ries et al. | 73/644 |
| 4,208,915 A | 6/1980 | Edwards | |
| 4,238,962 A | 12/1980 | Taenzer | |
| 4,252,125 A * | 2/1981 | Iinuma | 600/444 |
| 4,316,271 A | 2/1982 | Evert | |
| 4,332,016 A | 5/1982 | Berntsen | |
| 4,344,488 A | 8/1982 | Marks | |
| 4,517,985 A | 5/1985 | Teslawski et al. | |
| 4,518,992 A | 5/1985 | Kessler et al. | |
| 4,526,038 A | 7/1985 | Box et al. | |
| 4,543,130 A | 9/1985 | Shwartzman | |
| 4,662,215 A * | 5/1987 | Eckert | 73/61.75 |
| 4,781,067 A | 11/1988 | Cichanski | |
| 4,807,634 A | 2/1989 | Enjoji et al. | |
| 4,866,986 A | 9/1989 | Cichanski | |
| 4,920,803 A | 5/1990 | Karaki et al. | |
| 4,977,779 A | 12/1990 | Karaki et al. | |
| 5,014,711 A * | 5/1991 | Nagasaki | 600/443 |
| 5,060,517 A | 10/1991 | Fushimi et al. | |
| 5,117,697 A | 6/1992 | Takishita et al. | |
| 5,212,987 A | 5/1993 | Dransfeld et al. | |
| 5,301,552 A | 4/1994 | Nagura et al. | |
| 5,359,895 A | 11/1994 | Isenberg et al. | |
| 5,431,054 A | 7/1995 | Reeves et al. | |
| 5,469,742 A * | 11/1995 | Lee et al. | 73/597 |

(Continued)

*Primary Examiner*—Helen Kwok

(57) ABSTRACT

A method and apparatus for temperature-controlled ultrasonic inspection of an object. The temperature of a coupling medium between an ultrasonic transducer and an object under inspection is controlled to be at a predetermined temperature for which the attenuation of the ultrasonic energy in the coupling medium is reduced compared to the attenuation at an ambient temperature. This improves the efficiency of ultrasonic energy transport between the ultrasonic transducer and the object. The temperature of the object is controlled to simulate operating conditions more closely. An ultrasonic inspection system includes a temperature controller operable to maintain the temperature of the coupling medium and/or an object under inspection at a set temperature.

37 Claims, 3 Drawing Sheets

U.S. PATENT DOCUMENTS

| | | |
|---|---|---|
| 5,531,119 A | 7/1996 | Meyers |
| 5,585,564 A | 12/1996 | Brunty et al. |
| 5,600,068 A | 2/1997 | Kessler et al. |
| 5,629,865 A | 5/1997 | Roth |
| 5,646,351 A * | 7/1997 | Good et al. .................... 73/622 |
| 5,668,452 A | 9/1997 | Villarreal et al. |
| 5,684,252 A | 11/1997 | Kessler et al. |
| 5,922,961 A | 7/1999 | Hsu et al. |
| 5,948,985 A | 9/1999 | Brautigan et al. |
| 5,996,415 A * | 12/1999 | Stanke et al. .................. 73/597 |
| 6,062,084 A | 5/2000 | Chang et al. |
| 6,085,591 A | 7/2000 | Mallard |
| 6,089,095 A | 7/2000 | Yang et al. |
| 6,227,946 B1 | 5/2001 | Gonzalez-Martin et al. |
| 6,357,136 B1 | 3/2002 | Erickson et al. |
| 6,460,414 B1 | 10/2002 | Erickson et al. |
| 6,554,003 B1 | 4/2003 | Birang et al. |
| 6,880,387 B1 | 4/2005 | Kessler et al. |
| 6,890,302 B1 | 5/2005 | Oravecz et al. |
| 6,895,820 B1 | 5/2005 | Oravecz et al. |

* cited by examiner

METHOD AND APPARATUS FOR TEMPERATURE-CONTROLLED ULTRASONIC INSPECTION

PRIORITY CLAIM

This application claims priority from the provisional U.S. patent application titled "Method and Structure for the Efficient Delivery of Sonic Energy to Objects Undergoing SAM Inspection", filed Feb. 19, 2003 and identified by Ser. No. 60/448,622, which is hereby incorporated herein by reference.

FIELD OF THE INVENTION

This invention relates generally to the field of ultrasonic inspection. More particularly, this invention relates to an improved method and apparatus for temperature-controlled ultrasonic inspection.

BACKGROUND

Ultrasonic inspection methods, such as Scanning Acoustic Microscopy (SAM), provide valuable tools for the nondestructive inspection of microelectronic components and materials. By analyzing the ultrasonic response from a sample, the different interfaces and features of the sample can be verified. Also, flaws such as delaminations, cracks, voids, die tilt, underfill density variations and solder bump distortions can be detected. Ultrasonic analysis is usually performed by looking for changes in the amplitude or time-of-flight (TOF) of reflections in a high-frequency waveform signal (A-scan) of the sample at various locations (x, y) in the plane of the sample. By acquiring several A-scans along a line in this plane, a vertical cross-section image can be obtained. Also, by performing a raster-scan over the sample and only recording the amplitude or TOF from a certain depth within the sample at each location (x, y), a horizontal cross-section (C-scan) can be obtained. These images are easier to interpret than the set of A-scans, and are a common method for displaying ultrasonic data. More recently, full 3-dimensional renderings of a sample have become possible by recording the full A-scan at each location (x, y). These data sets allow for simulated scanning for efficient analysis, frequency-domain filtering to enhance of remove desired features, and F-scan imaging to bring out information that may be hidden in the time-domain signal.

All of these inspection methods currently rely upon the use of water to provide acoustic coupling between the ultrasonic transducer and the sample. The coupling may be provided by a flow of water from a dispenser or by immersion of the transducer and sample in a water bath. Typically, in the ultrasonic scanning of microelectronic parts, the water used for acoustic coupling is at ambient room temperature. However, the extent and shape of a flaw in a microelectronic sample may change when the sample is in use because the sample is at an elevated temperature.

The resolution of an ultrasonic scan is largely determined by the wavelength (frequency) of the ultrasound and the focusing ability of the ultrasonic transducer. However, the attenuation of ultrasound in the coupling medium between the transducer and the object being scanned increases rapidly with increasing frequency. Separations between the transducer and the object being scanned of much less than 0.5 mm are currently impractical in scanning acoustic microscopes. This separation sets an effective upper limit on the frequency of the ultrasound and consequently sets a limit on the spatial resolution that may be achieved in the ultrasonic scan.

SUMMARY

The present invention relates generally to improvements in ultrasonic inspection. Objects and features of the invention will become apparent to those of ordinary skill in the art upon consideration of the following detailed description of the invention.

In one embodiment of the invention, the temperature of a coupling medium between an ultrasonic transducer and an object under inspection is maintained at a predetermined temperature so as to facilitate efficient transport of ultrasound. In a further embodiment, the temperature of an object under inspection is maintained at a predetermined temperature so as to simulate the operating environment of the object more closely and facilitate identification of defects or other properties.

BRIEF DESCRIPTION OF THE DRAWINGS

The novel features believed characteristic of the invention are set forth in the appended claims. The invention itself, however, as well as the preferred mode of use, and further objects and advantages thereof, will best be understood by reference to the following detailed description of an illustrative embodiment when read in conjunction with the accompanying drawing(s), wherein:

DETAILED DESCRIPTION

Figure 1:
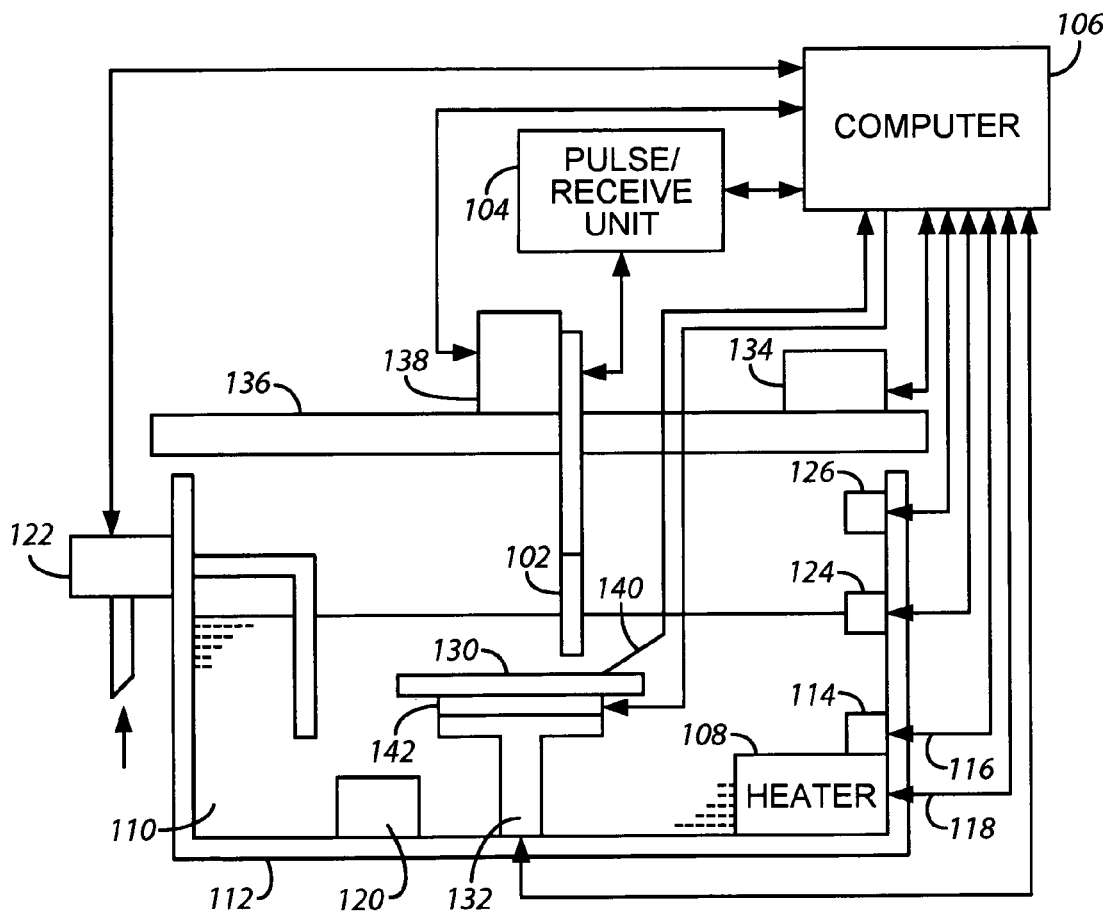
FIG. 1 is a diagrammatic view of an exemplary scanning acoustic microscope in accordance with certain aspects of the present invention.

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described. In the description below, like reference numerals are used to describe the same, similar or corresponding parts in the several views of the drawings.

One aspect of the present invention is a method for improving the efficiency of acoustic coupling between an ultrasonic transducer and an object. Acoustic coupling is usually provided by water. This may be achieved by immersion of the object under inspection (the object to be scanned) and the transducer in a bath of water, by using a dispenser (such as a 'bubbler' or a 'squirter') to create a flow of water between the transducer and the object under inspection or by creating a film of water between the transducer and the object under inspection. Acoustic coupling may also be provided by liquids other than water, by gels, or by solid, elastic materials. The efficiency of the acoustic coupling is determined by how much energy enters the coupling medium, by the attenuation of the acoustic wave within the medium and by the acoustic coupling between the medium and the object.

The attenuation of ultrasonic energy in a coupling medium between an ultrasonic transducer and an object under inspection is modeled by the factor $e^{-2\alpha x}$, where x is the distance traveled by the ultrasound within the coupling medium and $\alpha$ is an attenuation coefficient. To a good approximation, the value of attenuation coefficient increases with the square of the frequency and depends upon the physical properties of the coupling medium. Thus, it can be seen that to reduce attenuation, either the attenuation coefficient $\alpha$ or the propagation distance x (or both) should be reduced. Separations between the transducer and the object being scanned of much less than 0.5 mm are currently impractical in scanning acoustic microscopes. One aspect of the present invention is a method for reducing the attenuation coefficient, $\alpha$. Such a reduction allows for higher frequencies to be used (resulting in higher resolution) or for larger separations to be used. When the attenuation coefficient is reduced, the energy is transported more efficiently through the coupling medium.

Separations greater than 0.5 mm are typically preferred by users. Also, if the sample under inspection has packages placed close to objects of different heights (as on a populated circuit board), then a greater separation allows the transducer to pass over the other objects to get to the next package of interest. Additionally, an inspection area may be recessed into a sample (such as an optoelectronics device). A longer focal length is then required to avoid the transducer hitting the sides of the recessed area.

A diagrammatic view of an exemplary scanning acoustic microscope 100 of the invention is shown in FIG. 1. An ultrasonic transducer 102 is coupled to an ultrasonic receiver/pulse unit 104, which in turn is coupled to a computer 106. The computer 106 is used for control of the system and for the analysis, storage and display of ultrasonic data.

In one embodiment, a water heater 108 is used to heat water 110 in a reservoir or water bath 112. A temperature sensor 114 is used to measure the temperature of the water. The output 116 from the temperature sensor 114 is used by a temperature control mechanism (which may be implemented by the computer 106 or by a separate controller) to control the operation of the water heater 108 via control signal 118. The combination of the heater, sensor and control mechanism form a temperature controller for the coupling medium. In one embodiment, the temperature sensor 114 is a type K thermocouple probe and the water heater 108 is cartridge heater turned on and off by use of a relay controlled by the control signal. A water circulator 120 may be used to ensure an even temperature throughout the reservoir. The water circulator 120 may be integrated with the heater 108. The water heater may be positioned within the reservoir, as shown in FIG. 1, or positioned in a tube or pipe carrying water for recirculation.

The temperature sensor 114 may also be used to indicate if the water is over-temperature, and to trigger an emergency stop of the system. The emergency stop may switch the heater off or disconnect electrical power from the system. This prevents damage if, for example, the heater control mechanism fails.

In the embodiment shown in FIG. 1, the level of water 110 in the reservoir 112 is controlled by action of a water pump 122 that adds water to the reservoir when the water level, as measured by one or more level indicators 124, is below a predetermined level. Also, a level sensor 126 may be used to indicate over-filling of the reservoir and to trigger an emergency stop of the system. The emergency stop may disconnect electrical power from the system, for example. This prevents damage if, for example, the control mechanism of the water pump fails. The combination of the water pump, level sensors and control mechanism form a water level controller.

The object under inspection 130 is held in an object holder 132. For example, when the object under inspection is a semiconductor wafer, the object holder is typically a wafer chuck, such as a vacuum chuck, that is controlled to immerse the wafer in the reservoir of water. The wafer may be positioned on the chuck manually or by use of a robot arm.

The relative positions of the object under inspection 130 and the ultrasonic transducer 102 are adjusted along a scan-line by action of a first position controller 134 (such as linear-motor or a stepper-motor under control of the system computer 106) that moves the transducer along a track 136. The scan-line is horizontal in FIG. 1. A second position controller (not shown) adjusts the relative positions of the object under inspection 130 and the ultrasonic transducer 102 along a step-axis from one scan-line to the next. The scan-line may be a straight line or curved line. A third position controller 138 is used to adjust the distance of the ultrasonic transducer 102 from the object under inspection 130 along a focus-axis to facilitate focusing of the ultrasound to different depths within the object under inspection 130. The focus-axis is vertical in FIG. 1. The combination of the first, second and third position controllers form a transducer-position controller.

In an alternative embodiment, the ultrasonic inspection system allows the transducer to be moved about up to 6 axes so as to allow for the inspection of objects with more complicated geometries or to allow for variation of the angle of the transducer relative to the surface of the object. For example, the orientation of the transducer may be changed as the transducer is moved across the curved surface of an object. An example of such a system is a non-destructive testing system for the inspection of very small parts or surface coatings with very high frequency ultrasound. The ultrasonic inspection system may use one or more transducers to generate ultrasound in the object and may use one or more transducers to sense the ultrasound emitted from the object.

A second temperature sensor 140 may be used to measure the temperature of the object under inspection 130. A second heater 142 may also be used to heat the object under inspection 130. The second heater provides more rapid heating of the object under inspection than is obtained by just immersing the object in the water reservoir. It also provides for temperature control when the object under inspection is not immersed in the water. For example, when the acoustic coupling between the ultrasonic transducer and the object under inspection is provided by a flow of water from a dispenser, the object may have a steady-state temperature below that of the water. The second heater 142 may be incorporated into the object holder 132. The combination of the second heater, second temperature sensor and associated control mechanism form an object-temperature controller. When the object under test is a microelectronic device, it may be desirable to raise the temperature of the device to a temperature representative of an operating temperature of the device before the ultrasonic scan is performed.

In a further embodiment, the acoustic coupling medium is a solid medium that is held at an elevated temperature through surface heating.

In an implementation of a system of the present invention, a Scanning Acoustic Microscope was used to make A-scans and C-scans of a flip-chip sample. The part was placed in a bath of water and scans were made at various temperatures. The water provided the coupling medium. An ultra-high frequency transducer was used to generate an ultrasonic pulse and sense the ultrasonic pulse reflected from the part. At the ambient temperature (18° C.), the center frequency of the reflected pulse was 128.9 MHz. When the temperature of water increased, the attenuation decreased, yielding an increased in the strength of the reflected signal. Since the decrease in attenuation was higher at higher frequencies, the center frequency of the reflected pulse was shifted upwards in frequency. This provided improved resolution in the C-scan image of the microelectronic part. The speed of sound in the water also increased. The results are summarized in Table 1.

TABLE 1

| Temp. (° C.) | Sound speed (mm/µsec) | Change in Center Frequency (MHz) | Water Path Length (mm) | Change in Signal Strength |
|---|---|---|---|---|
| 18 | 1.483 | 0 | 3.1 | 0 dB |
| 28 | 1.83 | 16.6 | 3.95 | 6 dB |
| 38 | 1.879 | 29.3 | 4.0 | 10 dB |
| 48 | 1.9 | 32.23 | 4.1 | 12 dB |

In table 1, the water path length denotes the 'round-trip' water path length. In tests using lower frequency ultrasound, the measured increase in the sound speed was not as great. Also, standard measurements of the sound speed in pure water (at lower frequencies) do not show such a large increase. The reason for the extra increase has not been identified, but may be due to the use of drinking water rather than pure water in the water bath or to other changes within the system that appeared as a sound speed change.

Figure 2:
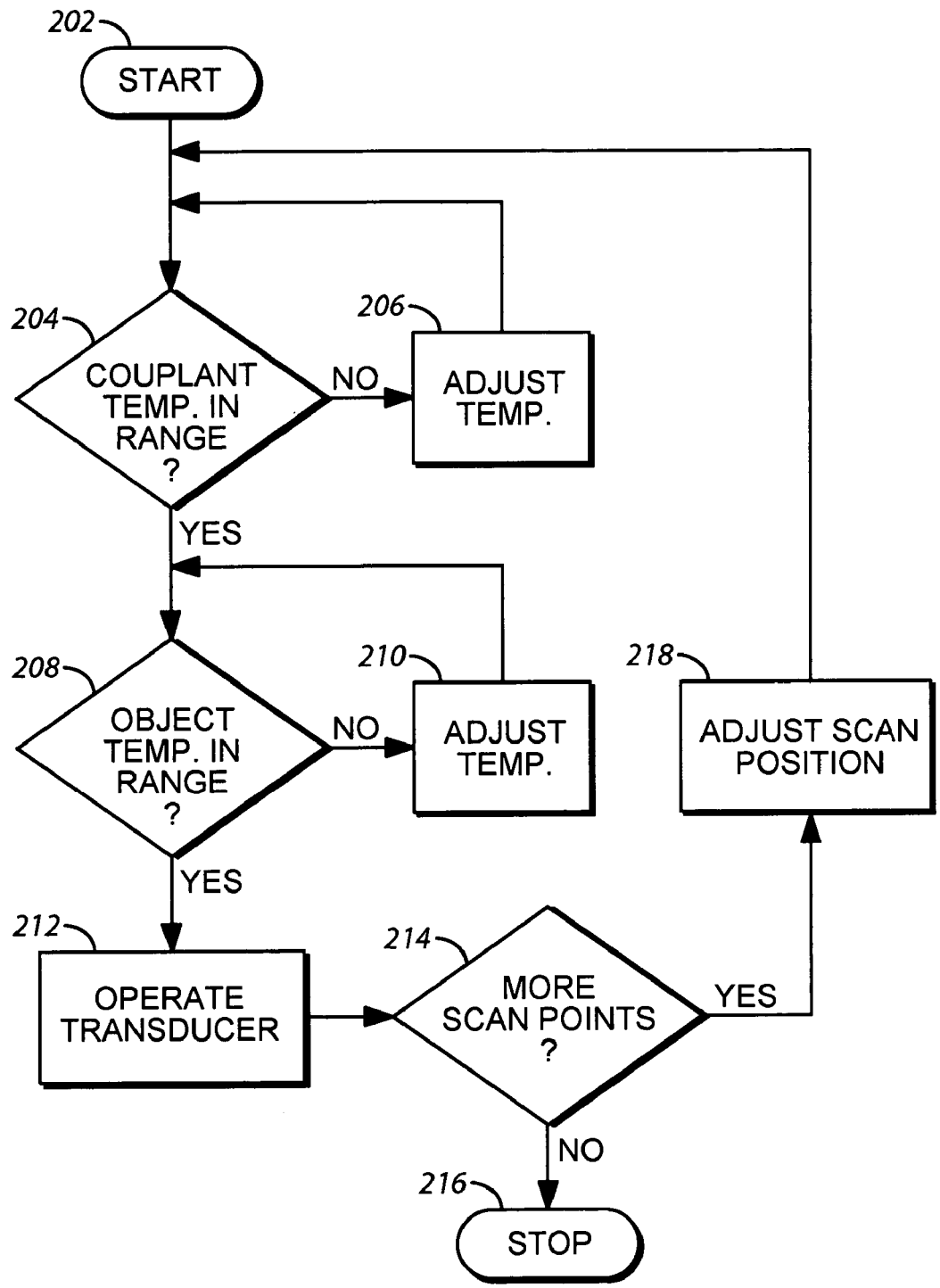
FIG. 2 is a flow chart depicting certain aspects of the method of the invention.

FIG. 2 is a flow chart depicting certain aspects of the method of the invention. Referring to FIG. 2, the method begins at start block 202. At decision block 204, a check is made to determine if the temperature of the coupling medium (the couplant) is within the predetermined temperature range. If the temperature of the coupling medium is outside of the predetermined temperature range, as depicted by the negative branch from decision block 204, the temperature of the coupling medium is adjusted at block 206. For example, if the temperature is too low, a heater is operated to raise the temperature, if the temperature is too high the coupling medium is allowed to cool. If the coupling medium is a liquid, cooler liquid may be added. If the temperature of the coupling medium is within the predetermined range, as depicted by the positive branch from decision block 204, flow continues to decision block 208.

At decision block 208, a check is made to determine if the temperature of the object under inspection is within the predetermined temperature range. If the temperature of the object under inspection is outside of the predetermined temperature range, as depicted by the negative branch from decision block 208, the temperature of the object under inspection is adjusted at block 210. For example, if the temperature is too low, a heater is operated to raise the temperature, if the temperature is too high the heater is switched off and the object is allowed to cool. If the temperature of the object under inspection is within the predetermined range, as depicted by the positive branch from decision block 208, flow continues to block 212. At block 212, the transducer is operated. If the system is a passive system, the transducer is activated to sense ultrasonic acoustic emissions from the object under inspection. For example, stresses may be applied to the object at this time to induce acoustic emissions. If the system is an active system, the transducer is activated to generate an ultrasonic pulse that propagates through the coupling medium and impinges on the object under inspection. The ultrasound reflected from or transmitted through the object under inspection is then sensed (either by the same transducer or an additional transducer). At decision block 214 a check is performed to determine if the object under inspection is to be scanned at additional scan points. If not, as depicted by the negative branch from decision block 214, the process terminates at block 216. If more points are to be scanned, as depicted by the positive branch from decision block 214, the scan position is adjusted at block 218, and flow continues to decision block 204. The scan position may be adjusted by moving the transducer, the object or both under the control of a scan controller (implemented by a computer for example). It will be apparent to those of ordinary skill in the art that temperature control of the coupling medium and/or the object may be performed by separate control systems that transmit signals to the scan controller to indicate if the corresponding temperature is within its predetermined range.

Figure 3:
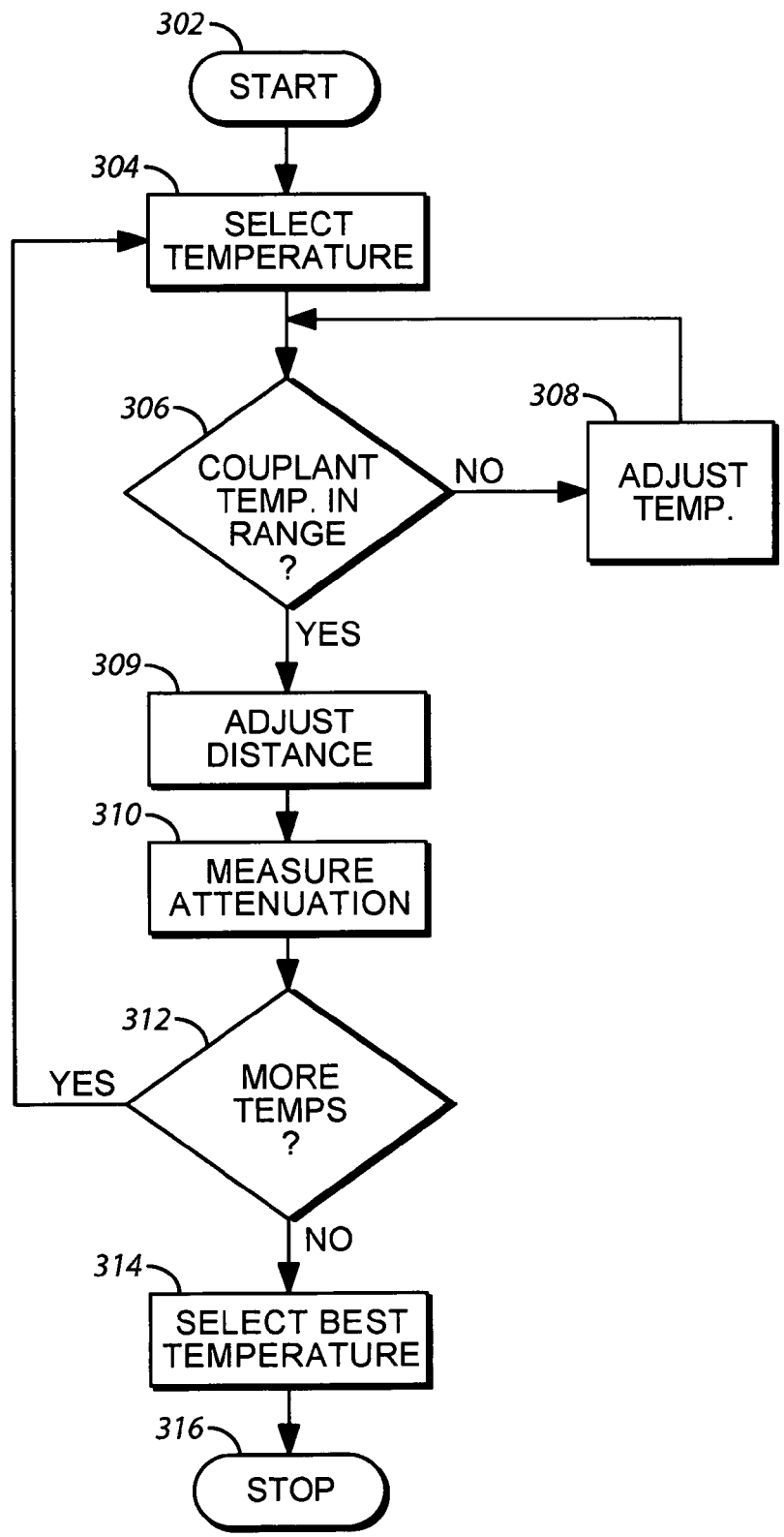
FIG. 3 is a flow chart depicting certain aspects of a further method of the invention.

FIG. 3 is a flow chart depicting an exemplary method for selecting the temperature of the coupling medium. Referring to FIG. 3, following start block 302, a temperature is selected from a list of temperatures. Preferably, the list of temperatures includes temperatures greater than the ambient temperature and less than the maximum operating temperature of the transducer. For example, the list may contain temperatures in the range 30° C.–50° C. At decision block 306 a check is made to determine if the temperature of the coupling medium (couplant) is within the predetermined temperature range. If the temperature of the coupling medium is outside of the predetermined temperature range, as depicted by the negative branch from decision block 306, the temperature of the coupling medium is adjusted at block 308. For example, if the temperature is too low, a heater is operated to raise the temperature, if the temperature is too high, the coupling medium is allowed to cool. For example, cooler water may be added when the coupling medium is water. If the temperature of the coupling medium is within the predetermined range, as depicted by the positive branch from decision block 306, flow continues to block 309 where, optionally, the acoustic path length is adjusted as necessary as the temperature is changed (so as to adjust signal strength or focus, for example). Flow continues to block 310, where the attenuation of the coupling medium is determined. This may be done, for example, by measuring the strength of an ultrasonic pulse with a fixed- or known-amplitude. At decision block 312, a check is made to determine if more temperatures are to be measured. If more temperatures are to be measured, as determined by the positive branch from decision block 312, flow returns to block 304 and the next temperature is selected from the list of temperatures. If no more temperatures are to be measured, as determined by the negative branch from decision block 312, the best temperature is selected based upon the attenuation at each temperature and other relevant factors. For example, if the lowest attenuation is achieved at a temperature close to the maximum permitted for the transducer, a slightly lower temperature may be selected. The process terminates at block 316.

The attenuation coefficient for a liquid is approximated by the expression $$\alpha = \frac{\omega^2}{2\rho_0 c^3}\left(\frac{4}{3}\eta + \eta_B\right),$$

where $\omega$, $\rho_0$ and $c$, respectively, are the radian frequency of the ultrasonic wave, the density of the liquid and the sound speed of the liquid, $\eta$ is the of shear viscosity and $\eta_B$ is bulk coefficient of viscosity. In general, the viscosities and the density decrease with increasing temperature, while the sound speed first increases and then decreases. The net result, as confirmed by experimentation, is a decreasing in attenuation with temperature. At lower frequencies the decrease in attenuation is small. However at very high frequencies the decrease in attenuation is significant, as described above.

The acoustic impedance of the coupling medium is also temperature dependent. The relationship between the impedance of the coupling medium and that of the transducer influence the ability of the transducer to couple acoustic energy into the coupling medium. As a result, the temperature selected for operation may also depend upon the properties of the ultrasonic transducer. For example, an ultrasonic transducer lens made of fused silica has a density=0.0022 g/mm$^3$ and a compressional sound speed $c_L$=5.95 mm/$\mu$s, so its characteristic acoustic impedance is $Z^L$=13.09×10$^{-3}$ g /(mm$^2$ $\mu$s). Water at 18° C. has a density=0.00099868 g/mm$^3$, and a sound speed c=1.483 mm/$\mu$s, giving a specific acoustic impedance $Z_W$=1.481×10$^{-3}$ g/(mm^2 $\mu$s). Water at 48° C. has a density=0.00098892 g/mm^3, and the sound speed was measured at ultrahigh frequency to be c=1.9 mm/$\mu$s, giving a specific acoustic impedance $Z_W$=1.879×10$^{-3}$ g/(mm$^2$ $\mu$s). The pressure transmission coefficient from the lens of the transducer to the coupling water is related to the impedances by T=2$Z_W$/($Z_L$+$Z_W$), so at 18° C., T=0.2, whereas at 48° C., T=0.25. This represents a 2 dB increase in signal strength.

The intensity transmission coefficient between the lens and the water (in either direction) is $T_I$=4$Z_W$ $Z_L$/($Z_L$+$Z_W$)$^2$. At 18° C., $T_I$=0.35, whereas at 48° C., $T_I$=0.422. This represents a 1.62 dB increase in the energy returned to the transducer due to the improved impedance matching. Thus the overall improvement in signal gain is due to the reduction in attenuation and the improved impedance matching.

These improvements are achieved because the impedance of the heated water is more closely matched to the impedance of the transducer lens. Similarly, the transmission coefficient between the coupling medium and the object under inspection may be enhanced by changing the impedance of the coupling medium to better match that of the object. This allows more ultrasonic energy to enter the object under test and more energy to be returned from the object under test to the coupling medium.

While the invention has been described in conjunction with specific embodiments, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims.

The invention claimed is:

1. An ultrasonic inspection system comprising:
   an ultrasonic transducer having an ultrasound emitting surface;
   a coupling medium acoustically coupled to the ultrasound emitting surface of the ultrasonic transducer and an object under inspection; and
   a first temperature controller operable to maintain the temperature of the coupling medium at a first temperature,
   wherein the ultrasonic transducer is operable to emit ultrasound having a center frequency greater than 100 MHz, and wherein the first temperature is selected to be a temperature at which attenuation in the coupling medium is reduced compare to attenuation in the coupling medium at ambient temperature.

2. An ultrasonic inspection system in accordance with claim 1, wherein the first temperature is higher than an ambient temperature and wherein the first temperature controller comprises a first heater and a first temperature sensor.

3. An ultrasonic inspection system in accordance with claim 1, wherein the coupling medium is water.

4. An ultrasonic inspection system in accordance with claim 3, wherein the water is stored in a reservoir.

5. An ultrasonic inspection system in accordance with claim 4, wherein the first temperature controller comprises a first heater, a first temperature sensor and a water circulator.

6. An ultrasonic inspection system in accordance with claim 4, further comprising a water level controller, operable to maintain the water at a predetermined level in the reservoir.

7. An ultrasonic inspection system in accordance with claim 1, further comprising a second temperature controller operable to maintain the temperature of the object under inspection at a second temperature.

8. An ultrasonic inspection system in accordance with claim 7, further comprising an object holder operable to hold the object under inspection, wherein the second temperature controller is integrated with the object holder.

9. An ultrasonic inspection system in accordance with claim 1, further comprising a second temperature sensor operable to sense the temperature of the object under inspection.

10. An ultrasonic inspection system in accordance with claim 1, further comprising a transducer-position controller operable to control the relative positions of the ultrasonic transducer and the object under inspection.

11. An ultrasonic inspection system in accordance with claim 1, wherein the coupling medium is water, further comprising a water dispenser operable to supply water to form an acoustic coupling between the ultrasound emitting surface of the ultrasonic transducer and the object.

12. An ultrasonic inspection system in accordance with claim 11, wherein the water dispenser receives water from a reservoir of water maintained at a predetermined temperature.

13. An ultrasonic inspection system in accordance with claim 11, wherein the first temperature controller is integrated with the water dispenser.

14. A method for efficient transport of ultrasonic energy between an ultrasonic transducer and an object under inspection, comprising controlling the temperature of a coupling medium between the ultrasonic transducer and the object under inspection to be at a first predetermined temperature for which the attenuation of the ultrasonic energy in the coupling medium at the first predetermined temperature is reduced compared to the attenuation of the ultrasonic energy in the coupling medium at an ambient temperature.

15. A method in accordance with claim 14, wherein the coupling medium is water.

16. A method in accordance with claim 15, wherein the first predetermined temperature is greater than 30° Celsius.

17. A method in accordance with claim 15, wherein the first predetermined temperature is greater than 35° Celsius and less than 50° Celsius.

18. A method in accordance with claim 15, wherein controlling the temperature of the coupling medium comprises:
sensing the temperature of the coupling medium; and
operating a first heater if the temperature of the coupling medium is below the first predetermined temperature.

19. A method in accordance with claim 18, wherein the water is contained in a reservoir and wherein controlling the temperature of the coupling medium further comprises circulating the water in the reservoir to maintain an even temperature distribution.

20. A method in accordance with claim 18, wherein the water is contained in a reservoir and further comprising controlling the level of water to be at a predetermined level in the reservoir.

21. A method in accordance with claim 14, further comprising:
sensing the temperature of the object under inspection; and
operating the ultrasonic transducer when the temperature of the object under inspection is substantially equal to a second predetermined temperature.

22. A method in accordance with claim 21, further comprising raising the temperature of the object under inspection when the temperature of the object is below the second predetermined temperature.

23. A method in accordance with claim 21, wherein the object is a microelectronic device and wherein the second predetermined temperature is representative of an operating temperature of the microelectronic device.

24. A method in accordance with claim 14, further comprising:
sensing the temperature of the coupling medium; and
operating the ultrasonic transducer when the temperature of the coupling medium is substantially equal to the first predetermined temperature.

25. A method in accordance with claim 24, wherein operating the ultrasonic transducer comprises the ultrasonic transducer sensing ultrasound emitted by the object.

26. A method in accordance with claim 24, wherein operating the ultrasonic transducer comprises:
the ultrasonic transducer generating an ultrasonic pulse into the coupling medium; and
the ultrasonic transducer sensing ultrasound emitted by the object in response to the ultrasonic pulse.

27. A method in accordance with claim 24, wherein operating the ultrasonic transducer comprises:
the ultrasonic transducer generating an ultrasonic pulse into the coupling medium; and
an additional ultrasonic transducer sensing ultrasound transmitted from the coupling medium through the object.

28. A method in accordance with claimed 24, wherein the ultrasound transducer is operated to generate an ultrasonic pulse having a center-frequency greater than 100 MHz.

29. A method for selecting a preferred temperature of a coupling medium in an ultrasonic inspection system, the method comprising:

(a) for each operating temperature of a plurality of operating temperatures:
controlling the temperature of the coupling medium to be approximately equal to the operating temperature;
energizing an ultrasonic transducer to generate an ultrasonic wave in the coupling medium; and
measuring the strength of the ultrasonic wave in the coupling medium; and (b) selecting the preferred temperature dependent upon the strengths of the ultrasonic wave at the plurality of operating temperatures.

30. A method in accordance with claim 29, wherein selecting the preferred temperature is also dependent upon a maximum operating temperature of the ultrasonic transducer.

31. A method in accordance with claim 29, wherein selecting the preferred temperature comprises selecting the operating temperature that maximizes the strength of the ultrasonic wave.

32. A method in accordance with claim 29, wherein the ultrasonic wave impinges upon an object and causes a reflected ultrasonic wave and wherein measuring the strength of the ultrasonic wave in the coupling medium comprises measuring the strength of the reflected ultrasonic wave.

33. A method in accordance with claim 29, further comprising adjusting the distance between ultrasonic transducer and the object for each operating temperature of a plurality of temperatures.

34. A method for ultrasonic inspection of an object having a predetermined operating temperature, the method comprising:
controlling the temperature of the object to be substantially equal to the predetermined operating temperature;
energizing a transducer to generate ultrasound in the object when the temperature of the object is substantially equal to the predetermined operating temperature; and
sensing the ultrasound emitted from the object.

35. A method in accordance with claim 34, wherein controlling the temperature of the object comprises:
sensing the temperature of the object; and
operating a heater if the temperature of the object is below the predetermined operating temperature.

36. A method for efficient coupling of ultrasonic energy between an ultrasonic transducer and an object under inspection, comprising controlling the temperature of a coupling medium between the ultrasonic transducer and the object under inspection to be at a first predetermined temperature, wherein the acoustic impedance of the coupling medium at the first predetermined temperature is better matched to that of the ultrasonic transducer compared to the acoustic impedance of the coupling medium at an ambient temperature.

37. A method in accordance with claim 36, wherein the coupling medium is water.

* * * * *